US010632026B2

(12) United States Patent
Ottery et al.

(10) Patent No.: US 10,632,026 B2
(45) Date of Patent: Apr. 28, 2020

(54) DISPOSABLE ABSORBENT GARMENT WITH IMPROVED ELASTICATION

(71) Applicant: ATTENDS HEALTHCARE PRODUCTS, INC., Greenville, NC (US)

(72) Inventors: Trenton T. Ottery, Delaware, OH (US); William W. Gaston, Greenville, NC (US); Richard E. Finlayson, Raleigh, NC (US); Brenda Roberson-Brown, Greenville, NC (US)

(73) Assignee: ATTENDS HEALTHCARE PRODUCTS, INC., Greenville, NC (US)

( * ) Notice: Subject to any disclaimer, the term of this patent is extended or adjusted under 35 U.S.C. 154(b) by 529 days.

(21) Appl. No.: 15/278,365

(22) Filed: Sep. 28, 2016

(65) Prior Publication Data

US 2017/0087031 A1 Mar. 30, 2017

Related U.S. Application Data

(60) Provisional application No. 62/233,899, filed on Sep. 28, 2015.

(51) Int. Cl.
*A61F 13/49* (2006.01)

(52) U.S. Cl.
CPC .. *A61F 13/49014* (2013.01); *A61F 13/49011* (2013.01)

(58) Field of Classification Search
CPC .......... A61F 13/49007; A61F 13/49009; A61F 13/49011; A61F 13/49012; A61F 13/49019; A61F 2013/49033; A61F 2013/49036
See application file for complete search history.

(56) References Cited

U.S. PATENT DOCUMENTS

| | | | | |
|---|---|---|---|---|
| 5,817,087 | A * | 10/1998 | Takabayashi | A61F 13/15203 604/385.29 |
| 6,375,646 | B1 | 4/2002 | Widlund et al. | 604/385.3 |
| 6,602,234 | B2 * | 8/2003 | Klemp | A61F 13/49012 604/385.01 |
| 7,632,259 | B2 | 12/2009 | Elfstrom et al. | 604/385.27 |
| 8,038,662 | B2 | 10/2011 | Hornung et al. | 604/385.3 |
| 8,092,440 | B2 | 1/2012 | Hermansson et al. | 604/385.27 |
| 2005/0267431 | A1 * | 12/2005 | Sasaki | A61F 13/49011 604/385.3 |
| 2015/0238368 | A1 * | 8/2015 | Mukai | A61F 13/496 604/385.24 |

* cited by examiner

*Primary Examiner* — Tatyana Zalukaeva
*Assistant Examiner* — Jessica R Arble
(74) *Attorney, Agent, or Firm* — Norton Rose Fulbright US LLP

(57) ABSTRACT

A disposable absorbent garment includes front and rear panels with zones of elastification and non-elastication in the abdomen and rear regions of the garments. The zones of elastification comprise an elastified region, and a non-elastified region or a de-elastified region. The elastified non-elastified or de-elastified regions work in tandem to provide greater contour support and improved fit.

16 Claims, 3 Drawing Sheets

244 230 212 220 226a 256 252 258 226b 240 246 224 236 254 248 234 228a 256 252 256 228b 222 232 214 244 216

DISPOSABLE ABSORBENT GARMENT WITH IMPROVED ELASTICATION

CROSS-REFERENCE TO RELATED APPLICATIONS

This application claims priority to U.S. Provisional Patent Application Ser. No. 62/233,899, filed Sep. 28, 2015, which is incorporated by reference in its entirety.

FIELD OF THE DISCLOSURE

The present invention relates generally to disposable absorbent garments with zones of elastication and non-elastication in the abdomen and rear regions of the garments.

BACKGROUND

Disposable absorbent garments contemplated by the invention include disposable diapers, disposable pull-on garments, and the like. These garments are worn about the lower torso or waist of the user so as to receive and contain urine and other bodily wastes. More preferably, disposable pull-on garments include training pants, pull-on diapers, protective underwear, and adult incontinence garments. Generally, the disposable absorbent garments are designed to be put on and taken off in the same manner by which regular underpants are put on and taken off.

The disposable absorbent garments include zones of elastication and non-elastication in the front and rear panels. The elasticated and non-elasticated regions work in tandem to provide greater contour support and improved fit. The zones of elastication work to mimic the contoured fit of regular underpants.

SUMMARY

It is one object of the present invention to provide an improved disposable absorbent garment such as a protective underwear or adult incontinence garment with zones of elastication and zones of non-elastication or de-elastication.

In accordance with one aspect of the present invention, a disposable absorbent garment is provided having a front panel, a rear panel, and a crotch panel. Moreover, the garment may include a longitudinally-extending, preferably elasticized, leg cuff spaced in generally parallel relation from each lateral side of the core. The leg cuffs may include an outer material, section or layer that is formed from the topsheet (e.g., topsheet side or outer section) and an inner material, and/or a section or layer that is substantially impervious.

In some embodiments, a disposable absorbent garment comprises a front panel, a rear panel, and a crotch panel that connects the front and rear panels. Each front and rear panel has two side edges, a waist edge end, and a crotch edge. In some embodiments, the crotch edges are curved at the sides to form leg openings. In other embodiments, the crotch edges are linear. The crotch panel comprises an absorbent core and connects the front panel with the rear panel. In some embodiments, the crotch panel comprises crotch elastics laterally outboard of the absorbent core. The crotch panel may comprise a multi-component absorbent core. In some embodiments, a crotch panel may comprise an acquisition layer, a distribution layer, a surge core, a storage core, one or more layers of tissue, a tissue wrap, and combinations thereof.

In some embodiments, a disposable absorbent garment comprises multiple elasticated areas. Elasticated areas may include the waist, abdomen, buttocks, leg openings, and crotch area. Elasticated areas may result from the inclusion of elastic strands, elastic film, or other elasticizing means known in the art. The waist elastics may comprise elastic strands that span along the entirety of the waist edges of the front and/or rear waist panels. The crotch elastics comprise elastic strands which span along the longitudinally-extending, laterally outboard edges of the crotch panel. In some embodiments, the crotch elastics travel the entire longitudinal length of the crotch panel. In other embodiments, the crotch elastics travel a portion of the longitudinal length of the crotch panel. In some embodiments, leg elastics comprise elastics that curve along the crotch edges of the front and rear waist panels. In some embodiments, the leg elastics begin at the panel side edges and extend laterally inwardly. In other embodiments, the leg elastics are located inward of the panel side edges. Leg elastics may travel across the entire width of the front and/or rear panels. In some embodiments, leg elastics do not travel over the crotch panel. In some embodiments, leg elastics are de-elasticized over all or a portion of the crotch panel. In some embodiments, leg elastics are relaxed over all or a portion of the crotch panel, particularly along the end regions of the crotch panel. In some embodiments, leg elastics travel over the absorbent core or, again, along the end regions of the crotch panel. In other embodiments, leg elastics do not travel over the absorbent core. In further embodiments, leg elastics are de-elasticized over the absorbent core. In some embodiments, the leg elastics run parallel to each other in a generally straight or curved manner, and do not come together, nor do they flare away from each other.

The disposable absorbent garments comprise regions of elastication or non-elastication, or zones of elastication in the abdomen and the rear or buttocks regions of the front and rear panels between the waist edge and the crotch edge of the garment. The regions comprise multiple elasticized regions, with the elastication of these regions resulting from the inclusion of elastic strands, elastic film, or other elasticizing means known in the art. The phrase "panel" region is used herein to refer to either or both of the front, abdomen region and/or the rear, buttocks region of the garment between the waist edge and the crotch edge. The phrase "elastics" is used herein to refer to any of the numerous means of known elastication. The panel elastication can assume a variety of configurations presenting multiple elasticized panel zones. In some embodiments, the panel elastics travel over the crotch panel or the ends thereof. In other embodiments, panel elastics do not travel over the crotch panel. In further embodiments, panel elastics are de-elastified over the crotch panel. In some embodiments, panel elastics are relaxed over the crotch panel.

As noted, the panel elasticated zones comprise regions of elastication and zones of de-elasticated or non-elasticated regions. The elasticated zones may be included in either or both of the front and rear panels of a disposable absorbent garment. In some embodiments, a disposable absorbent garment panel comprises a region of de-elastication, or a non-elasticated region, at either one or both of the longitudinal ends. In some embodiments, a region of de-elastication or a non-elasticated region runs along the entire width of the front and/or rear panel. In other embodiments, a region of de-elastication or a non-elasticated region runs along a fraction of front and/or rear panel width. In some embodiments, a region of de-elastication or a non-elasticated region is continuous. In other embodiments, a region of de-elastication or a non-elasticated region is discontinuous and comprises both de-elasticated or non-elasticated regions and elasticated regions. A region of de-elastication or non-elasticated region may be positioned just inward of a waist region. In some embodiments, a waist region may comprise waist elastics which are different from the remaining elastics. In other embodiments, a waist region may comprise waist elastics which are the same or essentially the same as the remaining elastics. In preferred embodiments, regions of de-elastication or non-elasticated regions along the panel width are substantially rectangular regions whose longitudinal dimension is less than its lateral dimension. In other embodiments, regions of de-elastication or non-elasticated regions along the panel width comprise non-rectangular shapes, including one or more lines, angled shapes, curved shapes, or irregular shapes.

In some embodiments, a disposable absorbent garment comprises regions of de-elastication or non-elasticated regions at the side edges of the front and/or rear panels. The regions of de-elastication or non-elasticated regions may run along a substantial portion of the length of the side edges, and in other embodiments, the regions constitute only a minor length of the side edge length. Regions of de-elastication or non-elasticated regions preferably are intermittent along the side edges. In some embodiments, regions of de-elastication or non-elasticated regions lie inward of side edge seams. In preferred embodiments, regions of de-elastication or non-elasticated regions along the side edges are substantially rectangular regions whose longitudinal dimension is larger than a lateral dimension. In other embodiments, regions of de-elastication or non-elasticated regions along the side edges comprise non-rectangular shapes, including one or more lines, angled shapes, curved shapes, or irregular shapes.

In some embodiments, a region of de-elastication or a non-elasticated region running along the entire width of the front and/or rear panel may be located inboard of front and/or rear panel longitudinal edges. The de-elastication or a non-elasticated regions present a gap in elastication of the panel elastics. Along the longitudinal direction of the panels, a region of panel elastics may be followed by a de-elasticated or non-elasticated region, which is then followed by an elasticated region. In some embodiments, a region of de-elastication or a non-elasticated region located inboard of front and/or rear panel longitudinal edges extends along a fraction of front and/or rear panel width. In some embodiments, a region of de-elastication or a non-elasticated region located inboard of front and/or rear panel longitudinal edges is continuous. In other embodiments, a region of de-elastication or a non-elasticated region located inboard of front and/or rear panel longitudinal edges is discontinuous and comprises both de-elasticated or non-elasticated regions and elasticated regions, for example, a dotted-line pattern. In preferred embodiments, regions of de-elastication or non-elasticated regions located inboard of front and/or rear panel longitudinal edges travel along the panel width and are substantially rectangular regions whose longitudinal dimension is less than a lateral dimension. In other embodiments, regions of de-elastication or non-elasticated regions located inboard of front and/or rear panel longitudinal edges travel along the panel width comprise non-rectangular shapes, including one or more lines, angled shapes, curved shapes, or irregular shapes.

The foregoing has outlined rather broadly the features and technical advantages of the embodiments of the present disclosure in order that the detailed description of these embodiments that follows may be better understood. Additional features and advantages of the embodiments of the present disclosure will be described hereinafter which form the subject of the claims of the present disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the present disclosure as set forth in the appended claims. The novel features which are believed to be characteristic of the present disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The following drawings illustrate by way of example and not limitation. For the sake of brevity and clarity, every feature of a given structure may not be labeled in every figure in which that structure appears.

DETAILED DESCRIPTION OF THE DRAWINGS

Figure 1:
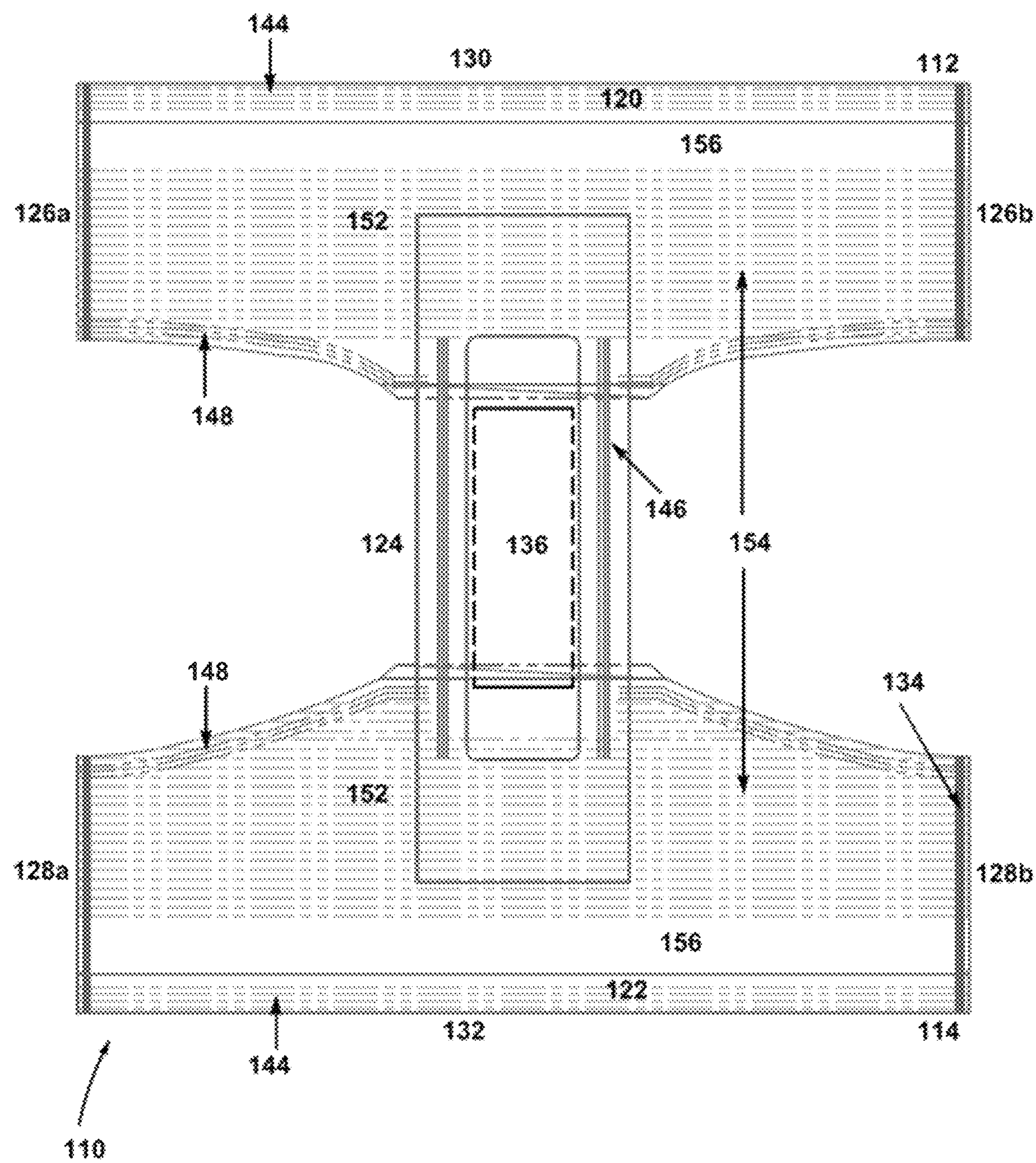
FIG. 1 is a top plan view of a disposable absorbent garment with laterally-extending non-elasticized or de-elasticized regions positioned inward of waist elasticized zones.

FIG. 1 depicts the disposable absorbent garment 10 in a flat and unfolded configuration, which it assumes during one point in the manufacturing process when it is stretched in both the lateral and longitudinal directions. As will be further explained below, the disposable absorbent garment 10 may be subsequently trimmed, folded, sealed, welded and/or otherwise manipulated to form a disposable absorbent garment 10 in final form and for packaging. In this regard, the disposable absorbent garment 10 is referred to as being finishable to form a final disposable absorbent garment product.

It should first be noted that, upon review of the detailed description and the drawings provided herein, it will become apparent to one of ordinary skill in the art that the present invention is also applicable to other disposable absorbent articles and, more particularly, to disposable absorbent garments other than protective underwear and adult incontinence garments.

Referring to FIG. 1, the garment 110 features a front panel 112 comprising front waist edge 130 and a rear panel 114 comprising rear waist edge 132. Crotch panel 124 connects front panel 112 and rear panel 114. The front panel, rear panel and crotch panels are preferably formed by joining two non-woven sheets, commonly referred to as a topsheet nonwoven, which faces the user and a backsheet nonwoven, which faces away from the user and faces the user's garment. The crotch panel includes an absorbent body positioned between the topsheet and backsheet as will be described in more detail below. Front panel 112 and rear panel 114 comprise front and back panel regions 120 and 122, respectively. Front panel region 120 abuts front waist edge 130, and comprises a portion of front panel 112. Rear panel region 122 abuts rear waist edge 132 and comprises a portion of rear panel 114. Front panel 112 comprises transversely opposite front side edges 126*a* and 126*b*. Rear panel 114 comprises transversely opposite rear side edges 128*a* and 128*b*. In the final disposable absorbent garment product, front and rear side edges 126*a* and 128*a* and front and rear side edges 126*b* and 128*b* are bonded together to form a three-dimensional absorbent garment comprising a waist opening and two leg openings. Particularly, front and rear side edges 126*a* and 128*a* and front and rear side edges 126*b* and 128*b* are bonded together to create side seams 134. Bonding of front and rear side edges may be accomplished by any means known in the art.

In some embodiments, transversely extending leg elastics 148 are positioned proximately to each crotch edge of front and rear panels 112 and 114. When the garment 110 is properly worn by the user, leg elastics 148 work in conjunction with each other and encircle the legs of the user and effects a seal thereon to prevent leakage. Generally, leg elastics 148 are formed with elastic members which are typically applied in the stretched or extended condition and are placed between the topsheet and backsheet. The elastic members are glued or otherwise secured to one or both of the topsheet or backsheet or other material layer of absorbent garment 110. Upon release from a stretched state, the elastic members retract with the attached material layer and form gathered leg regions surrounding leg openings of the final absorbent garment product.

As shown in FIG. 1, the disposable absorbent garment 110 may also be equipped with waist elastics 144. Waist elastics may be inserted between the topsheet and backsheet of each of the front and rear panels 112 and 114. In some embodiments, the waist elastics 144 may be omitted.

As mentioned above, when the garment 110 is properly worn about the waist region of the user, the topsheet generally contacts the user, while the backsheet faces outwardly from the body of the user. Further, the front waist region 120 of the garment 110 is situated at the front waist area of the user and the back waist region 122 is situated at the back waist area of the user, while the crotch region 124 is situated between the legs of the user and at the crotch area.

As used herein for the purpose of description, each of the terms "backsheet," "backsheet assembly" or "outer layer of the garment" refers to any sheet, layer or composite that is on the garment side of the undergarment and covers the core 136, and extends longitudinally beyond the core 136 toward the front and rear waist edges 130 and 132 and to side edges 126*a*, 126*b*, 128*a*, and 128*b*. Further, the term "backsheet," "backsheet assembly" or "outer layer of the garment" may refer to any assembly, unitary or integrally, of sheets, layers, or composites applied at least over the core 136 and any part, portion, region or section thereof. The backsheet and film material may be referred to as one structure or as individual structures or layers. For example, the backsheet may comprise three individual backsheets, one for each of front, rear, and crotch panels 112, 114, and 124. Alternatively, a unitary backsheet may be disposed on the back surfaces of front, rear, and crotch panels 112, 114, and 124.

The backsheet may be constructed from a number of different suitable materials and, preferably, may have a breathable or vapor-permeable attribute (distinguishing it from liquid-permeable) so that air can pass therethrough. The garment 10 may be equipped with a "nonwoven-poly assembly" comprising a nonwoven material of a hydrophobic, vapor-permeable material and a polyolefin film mask or film barrier that is laminated or otherwise applied onto the nonwoven material. In some embodiments, the film barrier may or may not be vapor-permeable. Preferably, the film barrier may be applied as a mask or sheet in a central area of garment 110. In some embodiments, the film barrier has an overall width that is less than the width of the other nonwoven materials but is sufficiently wide to cover the absorbent core.

One suitable construction for the backsheet assembly includes an outer layer of spunbond polypropylene fiber with a basis weight of about 15 gsm (available from BBA Nonwovens of Simpsonville, S.C.) and a polyethylene film of about 0.5 mil (0.0005") thickness adhesively laminated to the outer layer. Such a polyethylene film is available from, and manufactured by Exxon Chemical USA of Houston, Tex. The film may be laminated using adhesive available from National Starch & Chemical Company of Bridgewater, N.J. Yet another suitable construction for the backsheet 118 includes a web of spunbond or SMS (spunbond\meltblown\spunbond) nonwoven material and breathable or non-breathable films of 0.5 mils to 2.0 mils in thickness.

The absorbent core 136 is generally elongated and rectangular in shape. As best shown in FIG. 1, the core 136 is generally centered about the longitudinal and lateral axes of the garment 110. The core 136 is preferably made of an absorbent composition adapted to absorb bodily liquids received through the topsheet. Typically, the absorbent composition includes a fluffed wood pulp component for wicking and structural integrity and a high absorbency material (or super absorbent) for containing liquids. However, the garment 110, according to the present invention, is equally adapted to utilize absorbent cores of varying shapes and compositions, as well as other types of cores known in the art.

As used herein for purposes of description, the term "topsheet," "topsheet assembly" or "inner layer of the garment" may refer to any sheet, layer or composite that covers the core 136 and extends beyond the core 136 toward front and rear longitudinal edges 130 and 132 and towards side edges 126*a*, 126*b*, 128*a*, and 128*b*. Further, the term "topsheet," "topsheet assembly" or "inner layer of the garment" refers to any assembly, unitary or integrally, of sheets, layers, or composites applied over the core 136 and any part, portion, region or section thereof. The topsheet may be referred to as one structure or as individual structures or layers. For example, the topsheet may comprise three individual topsheets, one for each of front, rear, and crotch panels 112, 114, and 124. Alternatively, a unitary topsheet may be disposed on the front or wearer-facing surfaces of front, rear, and crotch panels 112, 114, and 124.

The topsheet may be constructed from a wide range of suitable materials including nonwoven webs of natural fibers (e.g., wood or cotton) or synthetic fibers (e.g., polypropylene or polyester), a combination of such webs or fibers, or apertured film. One suitable topsheet material is a 15 gsm spunbond polypropylene from Avgol Nonwoven Fabrics of Holon, Israel. In addition, the topsheet may be treated with a surfactant to facilitate liquid transfer, especially at a central zone of the topsheet over the core 136, and an inner surface of the topsheet may be treated with a chemical to increase the surface tension of liquid passing through the material.

Referring to the laid-open structure 110 of FIG. 1, the topsheet may comprise three topsheets, corresponding to a topsheet for each of front, rear and crotch panels 112, 114, and 124.

Leg cuffs may be positioned on either side of or spaced from a longitudinal center axis and laterally outboard of the core 136. These cuffs may extend generally upwardly from the topsheet (i.e., toward the user). The longitudinal ends of the cuffs may be attached, for example, to the topsheet in the front and rear panels 112 and 114. The ends of the leg cuffs may be tacked down inwardly and attached, for example, by adhesive. Such a construction biases the cuffs inwardly and is generally considered to cause the cuffs to exhibit improved leakage prevention properties.

The leg cuffs (or at least the outer cuff section) may be formed by a number of alternative methods known in the art. One method involves gluing a separately constructed leg cuff or cuff section to the top surface of the garment. Another method requires forming the leg cuff or cuff section from the topsheet or the backsheet. Yet another method involves creating and folding noodle cuffs as disclosed in U.S. Pat. No. 5,536,350, which is hereby incorporated by reference.

It is understood that it will be apparent to one skilled in the art, upon reading the detailed descriptions provided herein and viewing the accompanying Figures, to employ various conventional manufacturing elements (e.g., rollers, conveyors, etc.) and arrangements thereof to produce the garment and, more particularly, a breathable, stretchable section of the garment as described above.

Figure 2:
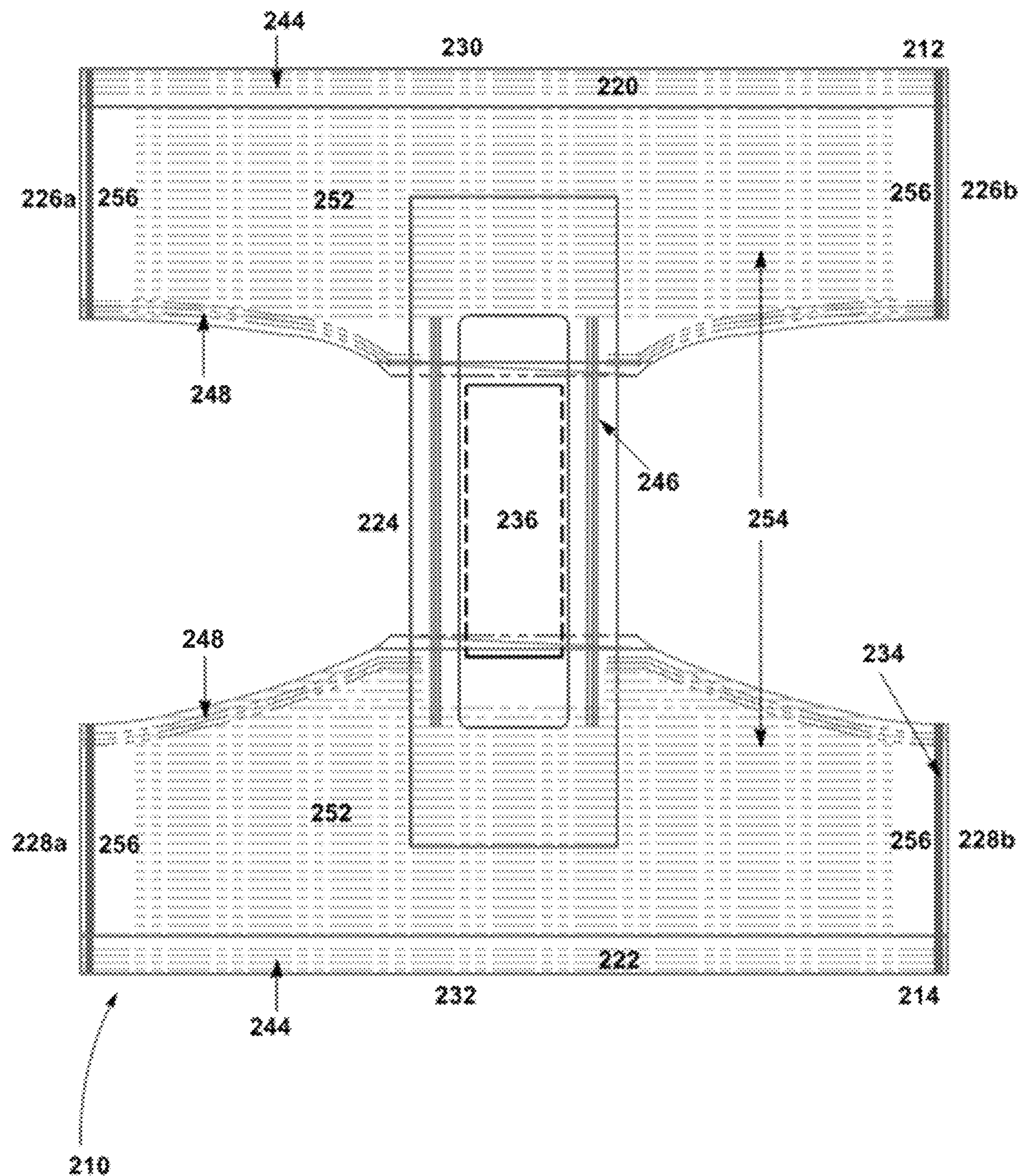
FIG. 2 is a top plan view of a disposable absorbent garment with vertical or longitudinal non-elasticized or de-elasticized regions inward of front and rear side edges and inward of side seams or edges.
Figure 3:
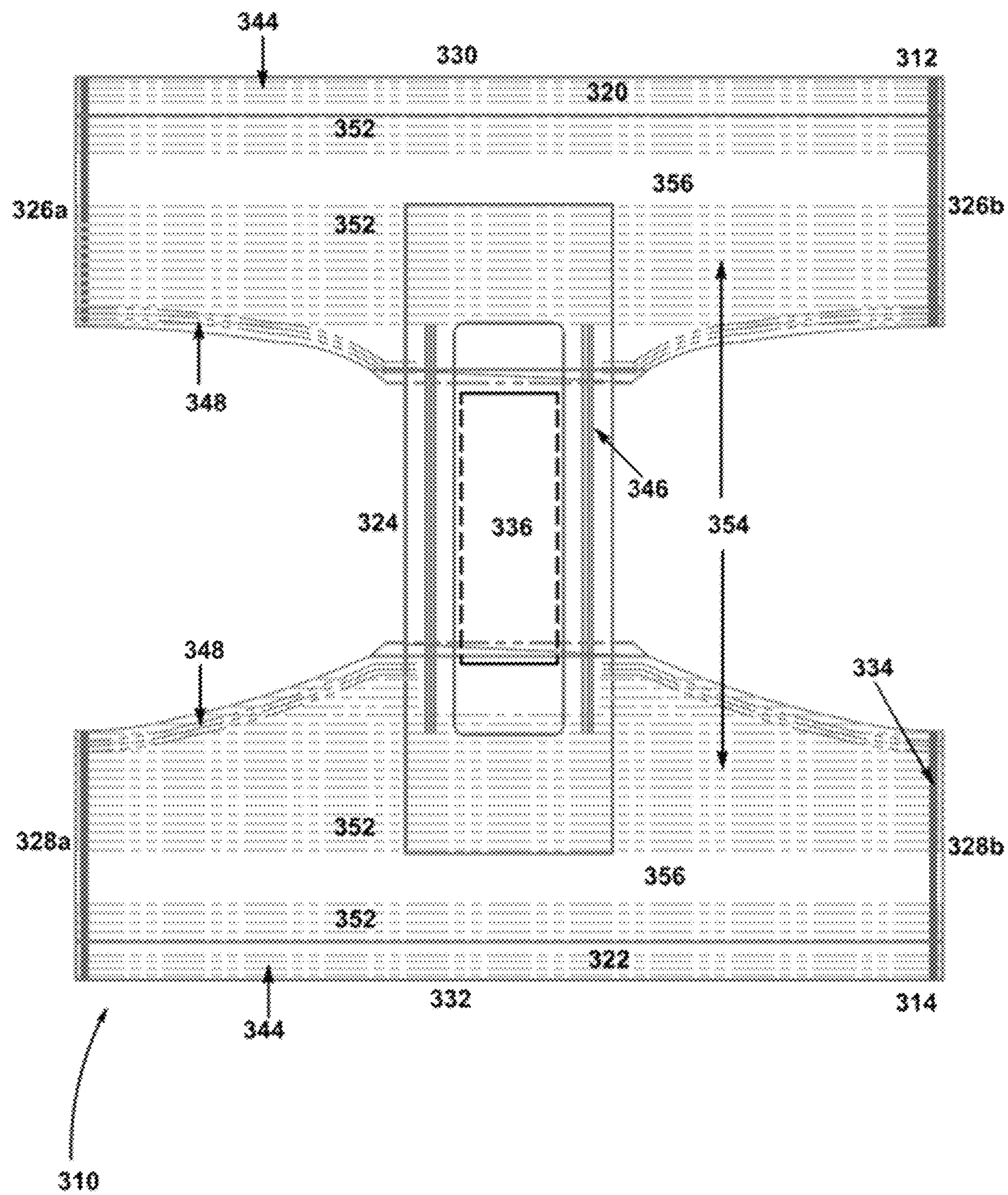
FIG. 3 is a top plan view of a disposable absorbent garment with laterally-extending non-elasticized or de-elasticized regions within front and rear panel elasticized areas.

Referring to FIG. 1, disposable absorbent garment 110 comprises multiple elasticated areas. Elasticated areas include the front and rear waist sections 120 and 122, panel elastics 154, leg elastics 148, and crotch elastics 146. The elastics depicted in the figures are elastic strands, however, other elasticizing means known in the art may be employed, for example, elasticated film. Referring to FIGS. 1-3, corresponding elements in respective garments 110, 210, and 310 are annotated so as to include the same final two digits. For example, crotch elastics are annotated as 146 in FIG. 1, 246 in FIG. 2, and 346 in FIG. 3. The absorbent core is annotated as 136 in FIG. 1, 236 in FIG. 2, and 336 in FIG. 3

Referring to the embodiment in FIG. 1, the front and rear panels 112 and 114 comprise elasticated zones comprising regions of elastication 152 and non-elasticated regions 156. For ease of reference, the term "non-elasticated" and variations of the term includes zones in which no elasticizing means is added and zones in which elasticizing means exist but have been de-elasticized, for example, a zone in which elasticized film exists but where the elastication of the film has been deadened or otherwise rendered ineffective. The non-elasticated regions 156 are located at front and rear longitudinal ends 130 and 132, inward of front and rear waist regions 120 and 122. Non-elasticated regions 156 traverse the entire lateral width of the front and rear panels 112 and 114. Non-elasticated regions 156 are continuous and are substantially rectangular in shape, with longitudinal dimensions being less than lateral dimensions.

Referring to the embodiment in FIG. 2, the front panel 212 comprises elasticated zones comprising a central region of elastication 252 and non-elasticated regions 256 at front panel 226*a* and 226*b*. In the embodiment illustrated, the regions of non-elastication 256 travel along the entire longitudinal length of the side edges 226*a* and 226*b*, except for the waist regions 220 and 222. Rear panel 214 comprises non-elasticated regions 256 at rear panel side edges 228*a* and 228*b*. In the embodiment depicted in FIG. 2, the side edge non-elasticated regions 256 are substantially rectangular regions with longitudinal dimensions that are larger than lateral dimensions.

Referring to the embodiment in FIG. 3, the front panel 312 comprises elasticated zones comprising a central region of elastication 352, upper elastication zones 352, and non-elasticated regions 356. The non-elasticated regions 356 travel along the entire width of the front and rear panels, and are laterally located within elasticated regions 352. The non-elasticated regions 356 present a gap within elasticated regions 352. In extending from the front waist edge 330 towards the crotch edge of front panel 312, a first region of waist elastics is followed by an upper zone of elastication 352, a non-elasticated region 356, which is then followed by a second region of panel elastics 352. In the embodiment depicted in FIG. 3, this pattern is repeated in the rear panel. In some embodiments, front and rear panel zones of elastication follow the same elastication pattern. In other embodiments, front and rear panel zones of elastification follow different patterns. For example, the front panel may comprise a longitudinally-spanning non-elasticized zone and the rear panel may comprise side edge non-elasticized zones. In still other embodiments, only one of the front and rear panels exhibit zones of elastication and non-elastication.

Additionally, the panel elastication may assume a variety of combinations of elasticized and non-elasticized zones. For example, the non-elasticized zones 156 of FIG. 1 may include intermittent, elasticized zones spaced inboard of the side edges and, likewise, the elasticized zones 152 may include intermittent, non-elasticized zones. The non-elasticized zones 256 of FIG. 2 may include intermittent, elasticized zones spaced inboard of the side edges and, likewise, the elasticized zones 252 may include intermittent, non-elasticized zones. The non-elasticized zones 356 of FIG. 3 may include intermittent, elasticized zones spaced inboard of the side edges and, likewise, the elasticized zones 352 may include intermittent, non-elasticized zones.

The claims are not to be interpreted as including means-plus- or step-plus-function limitations unless such a limitation is explicitly recited in a given claim using the phrase(s) "means for" or "step for," respectively.

Although the present disclosure and certain of its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A disposable absorbent garment comprising a front panel, a rear panel, and a crotch panel, where the front and rear panels comprises right and left side edges, and where the side edges of the respective panels are joined to form side seams, leg openings and a waist opening, and at least one of the front and rear panels comprises at least one elasticized zone and at least one non-elasticized zone, with at least a portion of the at least one non-elasticized zone being positioned along at least one of the side edges of the at least one front or rear panel, where the at least one non-elasticized zone comprises two non-elasticized areas each positioned along a respective side edge, where the at least one elasticized zone is disposed laterally between the two non-elasticized areas, where the at least one elasticized zone comprises a first elasticized area defined by longitudinal lines spaced inwardly of the side edges of the respective panel, a crotch edge of the respective panel, and a first laterally-extending line extending between the side edges of the respective panel and longitudinally spaced from a waist edge of the respective panel, and where the two non-elasticized areas are each defined by a longitudinally-extending line spaced inwardly of a respective side edge of the respective panel, a second laterally-extending line extending between the side edges of the respective panel, and a third laterally-extending line extending between the side edges of the respective panel and longitudinally spaced from the second laterally-extending line toward the crotch edge of the respective panel.

2. The disposable absorbent garment of claim 1, where the front and rear panels each include a respective first elasticized area and respective two non-elasticized areas.

3. The disposable absorbent garment of claim 1, where the second laterally-extending line is longitudinally spaced from the waist edge of the respective panel.

4. The disposable absorbent garment of claim 3, where the third laterally-extending line is aligned with at least a portion of the crotch edge of the respective panel.

5. The disposable absorbent garment of claim 1, where the third laterally-extending line is aligned with at least a portion of the crotch edge of the respective panel.

6. The disposable absorbent garment of claim 1, where the two non-elasticized areas include material of the front or rear panels.

7. The disposable absorbent garment of claim 1, where the front and rear panels each include respective first and second non-elasticized areas and a respective first elasticized area.

8. The disposable absorbent garment of claim 7, where the first and second non-elasticized areas each extend along an entire longitudinal length of the respective side edge except for a waistband region.

9. A disposable absorbent garment comprising a front panel, a rear panel, and a crotch panel, where the front and rear panels comprises right and left side edges, and where the side edges of the respective panels are joined to form side seams, leg openings and a waist opening, and at least one of the front and rear panels comprises at least one elasticized zone and at least one non-elasticized zone, with at least a portion of the at least one non-elasticized zone being positioned along at least one of the side edges of the at least one front and rear panel, where the at least one non-elasticized zone comprises two non-elasticized areas each positioned along a respective side edge, where the at least one elasticized zone is disposed laterally between the two non-elasticized areas, where the front and rear panels each include respective first and second non-elasticized areas and a respective first elasticized area, where a first end portion of the crotch panel overlaps a portion of the front panel, and a second end portion of the crotch panel overlaps a portion of the rear panel, and the at least one non-elasticized zone further includes a third non-elasticized area that includes at least the area of the front panel overlapped by the first end portion of the crotch panel, and a fourth non-elasticized area that includes at least the area of the rear panel overlapped by the second end portion of the crotch panel.

10. The disposable absorbent garment of claim 1, where the at least one elasticized zone includes a first elasticized area laterally extending from the left side edge to the right side edge of the respective panel along the width of the respective panel except for the two non-elasticized areas, and longitudinally extending along a portion of the side edges of the respective panel, and a second elasticized area that laterally extends along a crotch edge of the respective panel.

11. The disposable absorbent garment of claim 1, where the at least one elasticized zone includes a first elasticized area laterally extending from the left side edge to the right side edge along the width of the respective panel except for the two non-elasticized areas, and longitudinally extending along a portion of the side edges of the respective panel.

12. The disposable absorbent garment of claim 1, where a first end portion of the crotch panel overlaps a portion of the front panel, and a second end portion of the crotch panel overlaps a portion of the rear panel.

13. A disposable absorbent garment comprising a front panel, a rear panel, and a crotch panel, where the front and rear panels comprises right and left side edges, and where the side edges of the respective panels are joined to form side seams, leg openings and a waist opening, and at least one of the front and rear panels comprises at least one elasticized zone and at least one non-elasticized zone, with at least a portion of the at least one non-elasticized zone being positioned along at least one of the side edges of the at least one front and rear panel, where the at least one non-elasticized zone comprises two non-elasticized areas each positioned along a respective side edge, where the at least one elasticized zone is disposed laterally between the two non-elasticized areas, where a first end portion of the crotch panel overlaps a portion of the front panel, and a second end portion of the crotch panel overlaps a portion of the rear panel, and where the at least one elasticized zone does not extend over the crotch panel.

14. The disposable absorbent garment of claim 12, where the portion of the front panel overlapped by the first end portion of the crotch panel includes a third non-elasticized area distinct from the two non-elasticized areas.

15. The disposable absorbent garment of claim 14, where the portion of the rear panel overlapped by the second end portion of the crotch panel is not elasticized.

16. The disposable absorbent garment of claim 12, where the portion of the rear panel overlapped by the second end portion of the crotch panel is not elasticized.

* * * * *